US009623261B2

(12) United States Patent
Van De Wardt et al.

(10) Patent No.: US 9,623,261 B2
(45) Date of Patent: Apr. 18, 2017

(54) COMPONENTS AND ASSEMBLY FOR PERFORMING BRACHYTHERAPY TREATMENT OF TUMOUR TISSUE IN A HUMAN AND ANIMAL BODY

(75) Inventors: Cor Van De Wardt, Kesteren (NL); Emil Matthijs Buijs, Veenendaal (NL); Arie Luite Visscher, Driebergen (NL)

(73) Assignee: Nucletron B.V. (NL)

( * ) Notice: Subject to any disclaimer, the term of this patent is extended or adjusted under 35 U.S.C. 154(b) by 779 days.

(21) Appl. No.: 13/262,629

(22) PCT Filed: Mar. 22, 2010

(86) PCT No.: PCT/EP2010/001893
§ 371 (c)(1),
(2), (4) Date: Oct. 17, 2011

(87) PCT Pub. No.: WO2010/112172
PCT Pub. Date: Oct. 7, 2010

(65) Prior Publication Data
US 2012/0029263 A1    Feb. 2, 2012

(30) Foreign Application Priority Data
Apr. 1, 2009    (EP) .................................... 09004815

(51) Int. Cl.
*A61M 36/10*    (2006.01)
*A61N 5/10*    (2006.01)
(Continued)

(52) U.S. Cl.
CPC ............ *A61N 5/1016* (2013.01); *A61B 90/11* (2016.02); *A61M 25/01* (2013.01); *A61M 37/00* (2013.01);
(Continued)

(58) Field of Classification Search
CPC ....... A61N 5/1001–5/1029; A61N 2005/1008; A61N 2005/1009; A61N 2005/1012;
(Continued)

(56) References Cited

U.S. PATENT DOCUMENTS 4,998,912 A * 3/1991 Scarbrough et al. ............. 600/6
5,871,448 A * 2/1999 Ellard ........................... 600/459

FOREIGN PATENT DOCUMENTS

DE    44 13 489 C1    8/1995
EP    1 695 740 A1    8/2006
(Continued)

OTHER PUBLICATIONS

International Search Report from PCT/EP2010/001893, mailed Nov. 6, 2010 (3 pgs.).

*Primary Examiner* — Catherine B Kuhlman
(74) *Attorney, Agent, or Firm* — Finnegan, Henderson, Farabow, Garrett & Dunner, LLP

(57) ABSTRACT

The invention relates to an assembly for performing brachytherapy treatment of tumor tissue in a human or animal body comprising an intracavitary component and at least one guiding unit, said at least one guiding unit exhibiting a longitudinal axis and being connectable to said intracavitary component, and wherein said at least one guiding unit is provided with coupling means for coupling at least one interstitial needle-assembly for delivering treatment to said tumor tissue. The assembly has coupling/uncoupling means arranged to allow a displacement of said at least one interstitial needle-assembly in a direction transverse to said longitudinal axis and to prevent a displacement of said at least one interstitial needle-assembly in a direction parallel to or a pre-defined angle to said longitudinal axis. This coupling principle allows for the preparation of the guiding unit before the patient is being hospitalized and positioned in the treatment room and will prevent the unwanted uncou-
(Continued)

Figure 1:
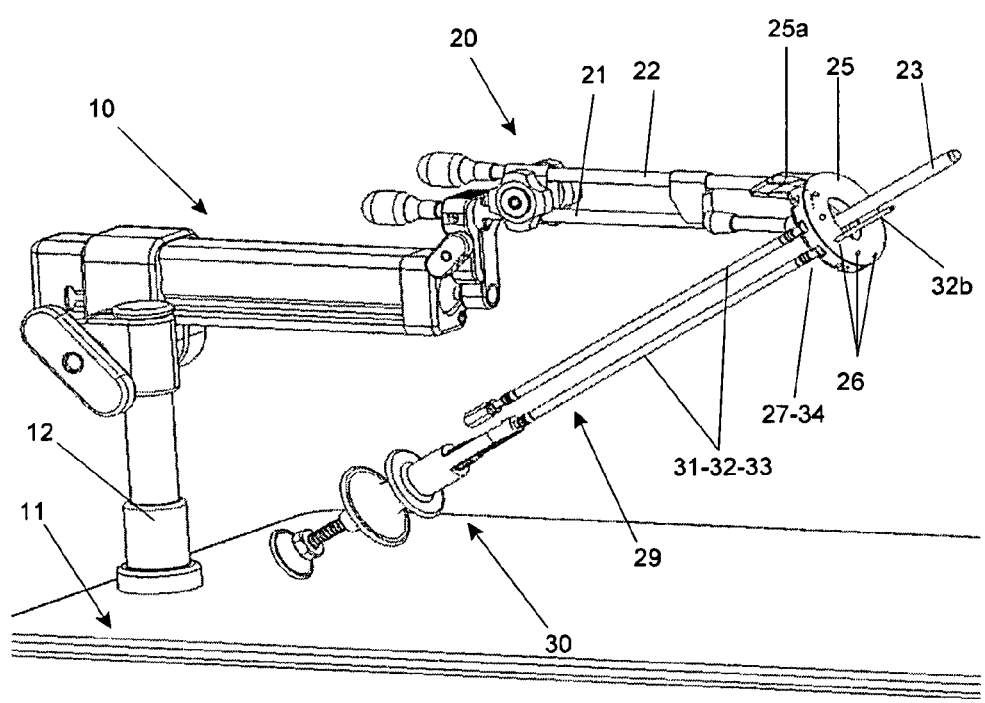

pling of the interstitial needle-assembly during the actual treatment being performed, further reducing the risk of adversely affected treatment parameters (location and duration of the radiation being administered to the patient).

11 Claims, 8 Drawing Sheets

(51) Int. Cl.
*A61M 25/01* (2006.01)
*A61M 37/00* (2006.01)
*A61B 90/11* (2016.01)
*A61B 17/42* (2006.01)
*A61B 17/34* (2006.01)

(52) U.S. Cl.
CPC ........ *A61N 5/1027* (2013.01); *A61B 17/4241* (2013.01); *A61B 2017/3411* (2013.01); *A61N 2005/1008* (2013.01); *A61N 2005/1012* (2013.01); *A61N 2005/1018* (2013.01)

(58) Field of Classification Search
CPC .......... A61N 2005/1018; A61N 5/1007; A61N 5/1014; A61N 5/1016; A61B 17/3403; A61M 5/1413; A61M 5/158; A61M 5/1582; A61M 5/3298; A61M 2005/1586; A61M 25/02; A61M 25/065; A61M 25/0102; A61M 2025/024; A61M 2025/028; A61M 37/0069
USPC ........................................................ 600/1–8
See application file for complete search history.

(56) References Cited

FOREIGN PATENT DOCUMENTS

WO    WO 2007/134126 A2    11/2007
WO    WO 2008/111070        9/2008

* cited by examiner

COMPONENTS AND ASSEMBLY FOR PERFORMING BRACHYTHERAPY TREATMENT OF TUMOUR TISSUE IN A HUMAN AND ANIMAL BODY

This application is a national phase application under 35 U.S.C. 371 based on International Application No. PCT/EP2010/001893, filed Mar. 22, 2010, which claims the priority of European Patent Application No. 09004815.8, filed Apr. 1, 2009, the entire contents of both of which are hereby incorporated by reference.

This invention relates to an assembly for performing brachytherapy treatment of tumour tissue in a human or animal body comprising an intracavitary component and at least one guiding unit, said at least one guiding unit being connectable to said intracavitary component, and wherein said at least one guiding unit is arranged in accommodating at least one interstitial needle-assembly for delivering treatment to said tumour tissue.

The invention also relates to an interstitial needle-assembly for performing brachytherapy treatment on tumour tissue in a human or animal body as well as a method for performing brachytherapy treatment of tumour tissue in a human or animal body using at least one energy emitting source to be positioned through a catheter channel near or in said tumour tissue with the aid of an interstitial needle-assembly.

Radiotherapy instruments as mentioned above and including interstitial needles are known in the medical field and are suitable for treatment of carcinoma of the cervix and/or endometrium. The insertion of additional interstitial needles makes it possible to create an optimized isodose curve for the treatment of tumours by using brachytherapy.

Known assemblies combine interstitial brachytherapy with intracavitary brachytherapy.

During interstitial brachytherapy treatment energy emitting (radioactive) sources are inserted into the tumourous tissue of the human or animal body to be treated, whilst during intracavitary brachytherapy treatment radioactive sources are inserted inside a pre-existing body cavity. With interstitial and intracavity brachytherapy an active energy emitting source is used to administer what is generally known as High Dose Rate (HDR) treatment. In HDR treatment the radiation source is guided into the tissue or cavity for one or more periods by means of a needle or catheter and is always contained within a closed capsule so it never comes into direct contact with the tissue. Brachytherapy can also be performed with PDR (pulse dose rate), or LDR, (low dose rate) treatments. The assemblies and components described herein would be suitable for administration of all types of Brachytherapy.

In the known assemblies an intracavitary component is inserted first with the distal end in a patient's body cavity. Next, one or more interstitial needles are connected to the guiding unit according to the therapy treatment to be performed.

Usually the interstitial needles are to be guided through suitable guiding holes or openings present in the guiding unit. Coupling multiple interstitial needles to the guiding unit as such requires significant skill and time prior to the actual radiation treatment to be performed, during which time the patient is already on the treatment table thus discomforting the patient. There is a risk when trying to guide the interstitial needles to the holes or openings in the guiding unit of causing unwanted damage or injury to the wall of the patient's body cavity, and possibly even a risk of puncturing it. Also the way interstitial needles are coupled to the known device has the drawback of a risk of an unintentional (and unwanted) uncoupling of the interstitial needle from the guiding unit. This could result in a relocation of the catheter channel relative to the tumour tissue to be treated, and therefore adversely affecting the treatment parameters for said patient.

It is therefore an object of the present invention to provide an improved assembly for performing brachytherapy treatment of tumour tissue in a human or animal body comprising an intracavitary component and at least one guiding unit, said at least one guiding unit exhibiting a longitudinal axis and being connectable to said intracavitary component, and wherein said at least one guiding unit is provided with coupling means for coupling to at least one interstitial needle-assembly for delivering treatment to said tumour tissue, wherein the interstitial needle-assembly comprising a guidance channel through which a hollow catheter channel is movable along said longitudinal axis, wherein the hollow catheter channel is capable of extending beyond the guiding unit and the guidance channel into said tumour tissue for delivering treatment to said tumour tissue.

An assembly according to the present invention at least partly mitigates some of the disadvantages of the prior art by providing a guidance channel along which the hollow catheter can be moved both relatively easily and safely.

It is a further object of the present invention to provide an assembly for performing brachytherapy treatment of tumour tissue in a human or animal body comprising an intracavitary component and at least one guiding unit, said at least one guiding unit exhibiting a longitudinal axis and being connectable to said intracavitary component, and wherein said at least one guiding unit is provided with coupling means for coupling at least one interstitial needle-assembly for delivering treatment to said tumour tissue, wherein for coupling/uncoupling purposes said coupling means are arranged to allow a displacement of said at least one interstitial needle-assembly in a direction transverse to said longitudinal axis and to prevent a displacement of said at least one interstitial needle-assembly in a direction parallel to said longitudinal axis. This improved assembly has an advantage of exhibiting a more efficient coupling principal and significantly reducing the preparation time prior to the actual treatment, thereby reducing any discomfort to the patient and moreover further limiting the risk of an undesired uncoupling of said interstitial needle-assembly during the actual treatment being performed.

This preparation time is reduced because the insertion of the guiding unit and needle-assemblies is made much easier and quicker.

A further reduction in the preparation time of the assembly prior to the actual treatment is achieved as in a further embodiment the guidance channel has a distal end which is releasably connectable to the guiding unit.

In order to avoid an unintended displacement of the catheter channel relative to the guidance channel and the tumourous tissue to be treated and thus adversely affecting the treatment parameters the guidance channel has a proximal end provided with means to secure the hollow catheter channel against movement along the longitudinal axis.

An advantage of an assembly according to the invention is the coupling/uncoupling steps are arranged by allowing a displacement of said at least one interstitial needle-assembly in a direction transverse to said longitudinal axis and prevented in a displacement of said at least one interstitial needle-assembly in a direction parallel to said longitudinal axis.

This coupling principle allows for the preparation of the guiding unit before the patient is positioned in the treatment room. Moreover this will prevent the unwanted uncoupling of the interstitial needle-assembly during the actual treatment being performed, further reducing the risk of adversely affected treatment parameters (location and duration of the radiation being administered to the patient).

Alternatively, the releasable connection means between the guiding unit and guidance channel are cooperating screw thread means, whereas in another alternative embodiment the releasable connection means between the guiding unit and guidance channel are bayonet fitting means.

In an advantageous embodiment the guidance channel is made from a flexible plastics material.

More in particular said at least one guiding unit is provided with at least one recess for accommodating, during use, at least part of said at least one interstitial needle-assembly. Accommodating a part of the interstitial needle-assembly in a recess instead of guiding it through a guidance opening has considerable advantages when treating the patient, as the guiding unit can be pre-assembled with multiple interstitial needle-assemblies before the assembly is to be inserted into the patient's body (or cavity).

Since the guiding unit already has all the interstitial needle-assemblies that are planned or needed installed (or in place) or pre-assembled on it, the time and difficulty of inserting the guiding unit is significantly reduced and any discomfort to the patient is reduced, and treatment can be started much more quickly when compared to existing or known systems.

Each recess is provided in the circumferential surface of said guiding unit resulting in an easy and quick mounting of the interstitial needle-assemblies prior to the actual treatment and dismounting once the treatment has been performed.

More in particular said interstitial needle assembly comprises a guidance channel having a distal end, which distal end is to be accommodated in said recess. This allows a pre-preparation of the guiding unit prior to the actual treatment by accommodating multiple guidance channels in corresponding recesses, thereby reducing the waiting time for the patient prior to the actual treatment.

In an improved embodiment said distal end of said guidance channel is provided with a connection element fitting said recess. More in particular said recess comprises at least a first recess part, which continues in a second recess part and wherein said connection element is provided with at least a first element part fitting said first recess part as well as a second element part fitting said second recess part.

The recess parts of the recess in the guiding unit cooperate with corresponding element parts of the connection element of the guidance channel to limit the amount of longitudinal axial movement of the guiding tube. The connection element of the guidance channel may either be integrally moulded or formed as part of the guidance channel, or alternatively it could be a separate component which is engaged with or inserted into the guide tube.

In order to allow a proper insertion of the interstitial needle-assemblies said recess continues in a guiding bore running through said guidance unit. The guiding bore serves for guiding a catheter channel running through said guidance channel.

In a first embodiment said guiding unit has an annular or ring shape surrounding said intracavitary component. This allows a proper connection of multiple interstitial needle-assemblies, which allows in creating an optimized isodose curve for the treatment of tumours by using brachytherapy.

Likewise in another embodiment said guiding unit has an ovoid shape abutting said intracavitary component. Due to the shape of such guiding unit, it is pressed against the cervix tissue wall and creates a space around the healthy tissue.

More particularly said shaped guiding unit is provided with at least one groove for accommodating said intracavitary component. This improves and simplifies the mounting and dismounting of the assembly for performing brachytherapy treatment in the patient's body.

The invention also relates to an interstitial needle-assembly for performing brachytherapy treatment of tumour tissue in a human or animal body comprising:

a hollow guidance channel having a proximal guidance channel end and a distal guidance channel end, wherein during use said distal guidance channel end is to be positioned in the human or animal body close to or in the tumour tissue, a hollow catheter channel having an open proximal end and a closed distal end for insertion through said guidance channel towards a position in or near said tumour tissue, as well as a support wire having a proximal end and a distal end and being removably accommodated in said catheter channel for supporting said catheter channel through said guidance channel towards said position in or near said tumour tissue.

It is an aim of the present invention to provide such interstitial needle-assembly as mentioned above, wherein the displacement and especially the insertion depth of each catheter channel inside the patient's body can be automated and adequately (and accurately) controlled.

According to the invention said interstitial needle-assembly further comprises an insertion unit for inserting said hollow catheter channel and said support wire from outside the patient through said guidance channel towards said position in or near said tumour tissue.

Said insertion unit comprises a housing arranged for accommodating the proximal end of said guidance channel and wherein said proximal end of said guidance channel is provided with a connection element fitting said housing of said insertion unit. This allows for an accurate placing of the hollow catheter channel by means of the insertion unit together with the support wire at a certain pre-determined distance (or depth) inside the patient.

In a further improved embodiment said connection element is configured as a means for securing or fixing said catheter channel relative to said guidance channel. This prevents an unwanted shifting of the catheter channel inside said guidance channel, once the catheter channel has been inserted to its desired depth (as pre-planned) inside the patient's body. This shifting may adversely affect the treatment to be performed.

In order to accurately displace the catheter channel though the guidance channel according to an embodiment of the invention said insertion unit comprises an insertion plunger movable accommodated in said housing for displacing said hollow catheter channel and said support wire through said guidance channel.

For a proper setting of the insertion depth of the catheter channel according to the treatment parameters of the brachytherapy treatment to be performed in an embodiment said insertion plunger is provided with a setting notch for setting the displacement of said plunger through said housing. More in particular said setting notch is constructed as a setting nut having an internal screw thread cooperating with an external screw thread provided on said insertion plunger.

The invention also relates to a method for performing brachytherapy treatment of tumour tissue in a human or animal body using at least one energy emitting source to be positioned through a catheter channel near or in said tumour tissue with the aid of an interstitial needle-assembly according to the invention.

Figure 2A:
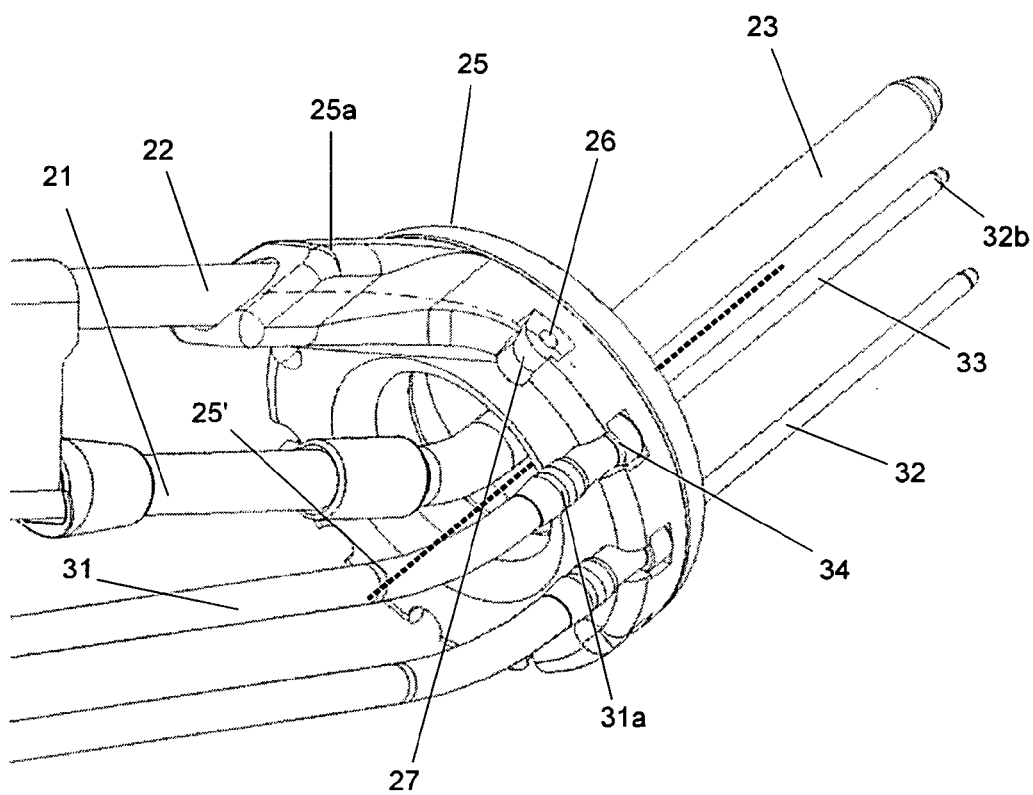
Figure 2B:
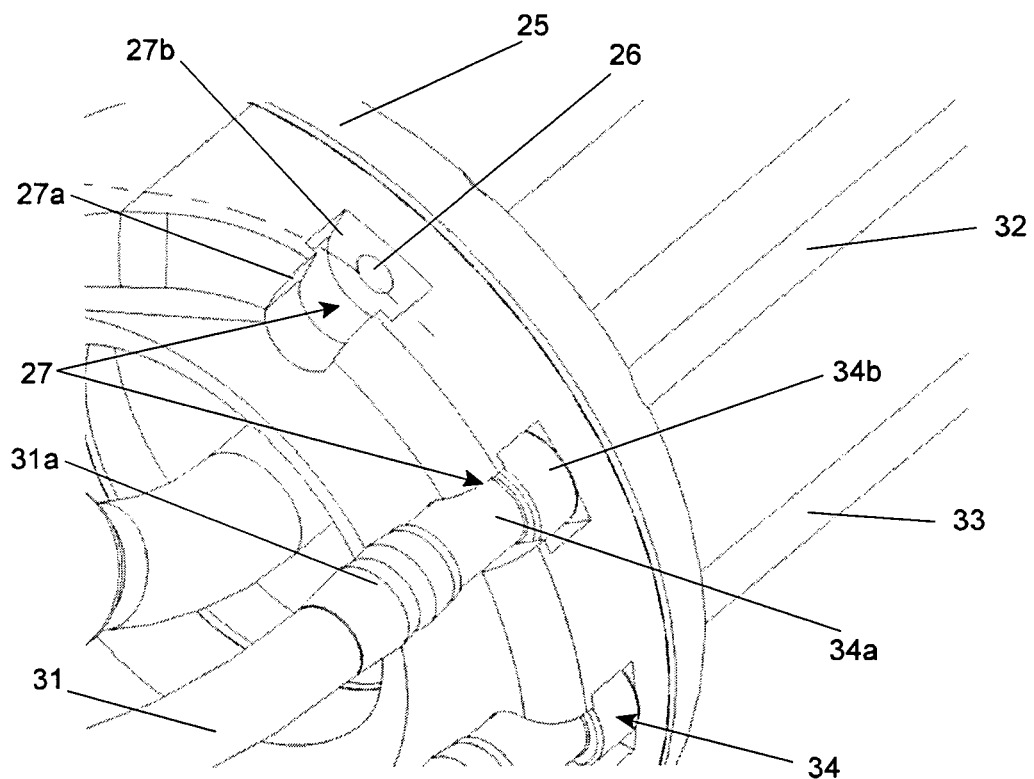
Figure 3A:
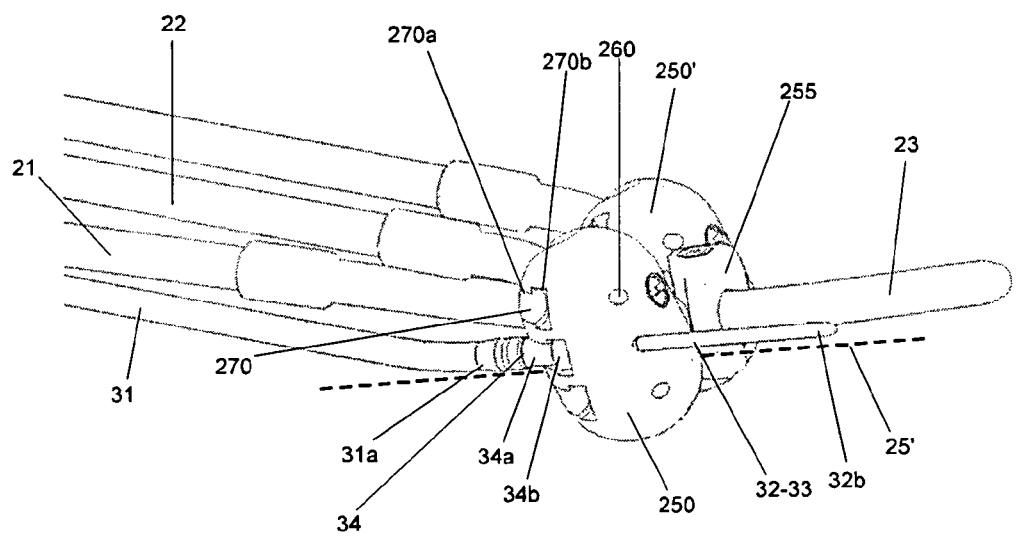
Figure 3B:
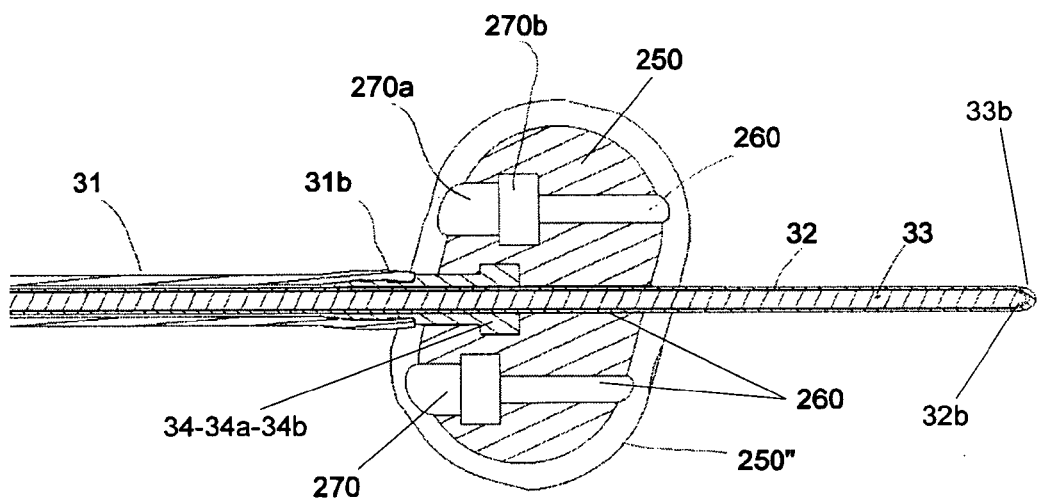
Figure 4:
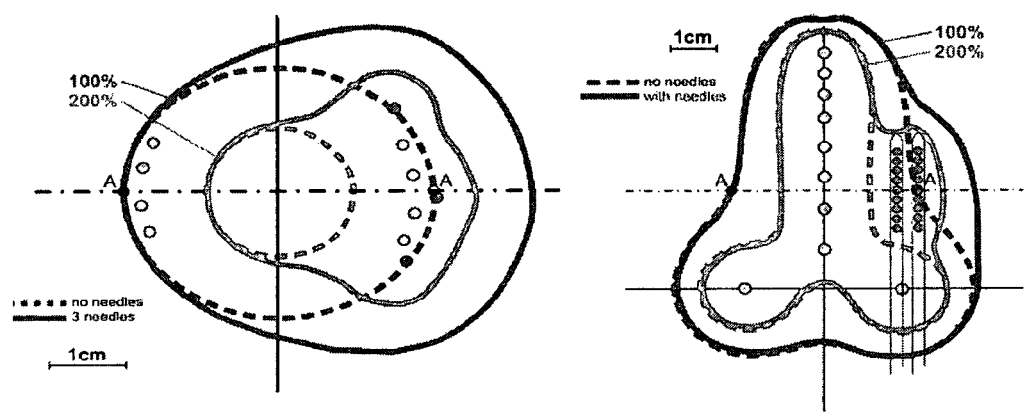
Figure 5:
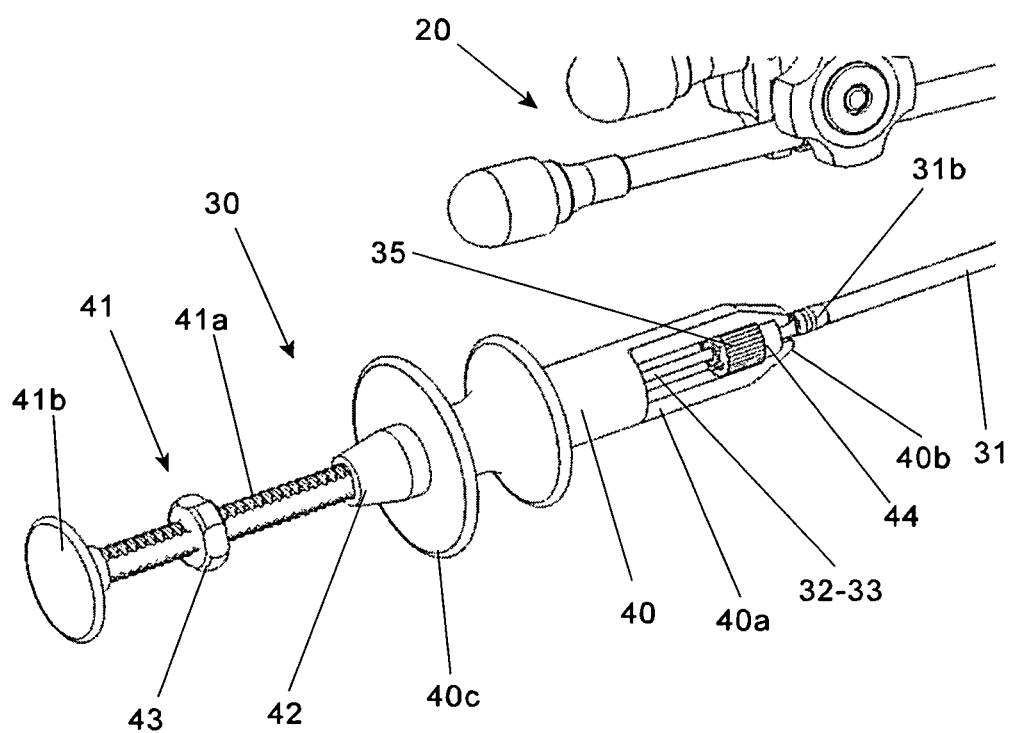
Figure 6:
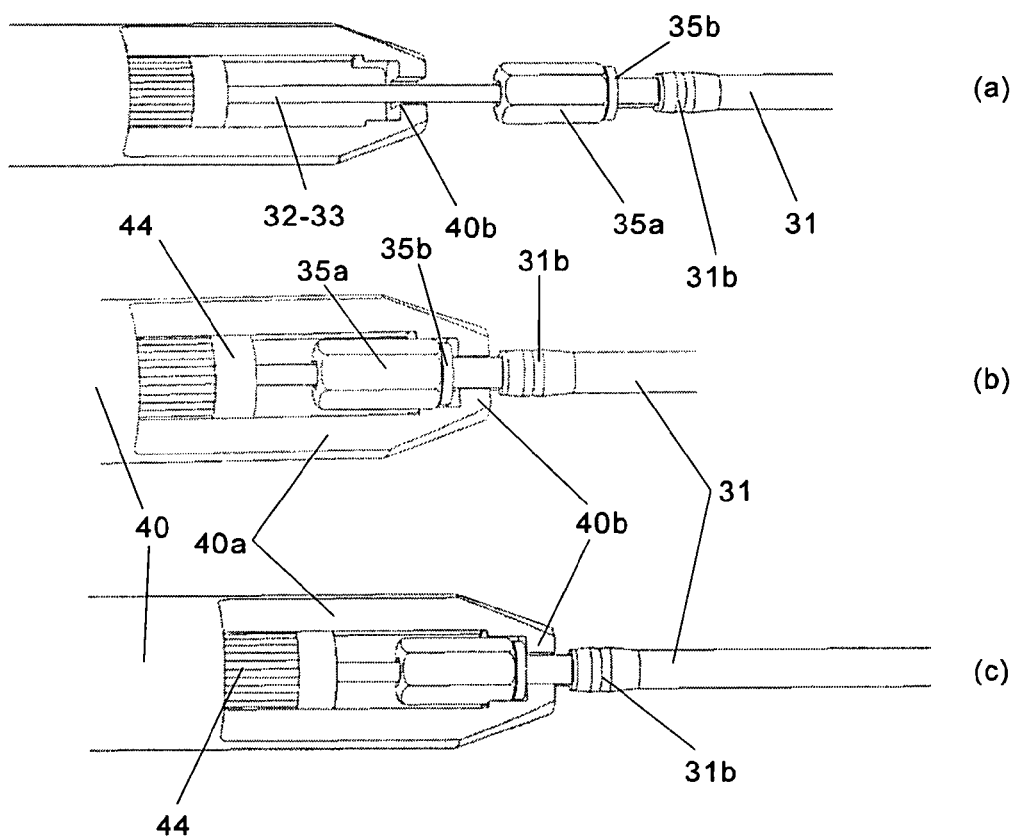

The invention will now be described in more detail with reference to a drawing, which drawing shows in:

FIG. 1 a first embodiment of an assembly according to the invention;

FIGS. 2a-2b detailed views of the embodiment of FIG. 1;

FIGS. 3a-3b a second embodiment of an assembly according to the invention;

FIG. 4 schematic views of a target location inside a human or animal body;

FIG. 5 an embodiment of an interstitial needle-assembly according to the invention;

FIGS. 6a-6c detailed views of FIG. 5.

FIG. 1 discloses an embodiment of an assembly according to the invention. Reference numeral 11 denotes a treatment table on which a female patient to be orientated in lithomony position. The treatment table 11 is provided with a support 12 on which a mounting apparatus 10 is attached. Mounting apparatus 10, which function is not relevant for the present invention, serves to orientate a medical tool relative to a patient's body, depending on the medical treatment to be performed.

In FIG. 1 mounting apparatus 10 (or clamping apparatus 10) holds a part of an embodiment of an assembly according to the present invention in a clamping fashion.

The assembly according to the present invention comprises an intracavitary component 20 and at least one guiding unit 25, which is connectable to said intracavitary component 20. The intracavitary component 20 consists of at least one (here two) support tubes 21 and 22 respectively. The first support tube 21 continues in an intrauterine tube 23 which can be inserted with its free distal end in a body cavity, for example into the uterus in the direction of the cervix. The other support tube 22 supports the guiding unit 25, which according to the invention is to be positioned inside the vagina, with ring-shaped element 25 pressed against the cervix.

In the embodiment shown in FIG. 1 (and also in FIGS. 2a and 2b) the guiding unit 25 consists of an annular or ring-shaped element 25 which is positioned around the intrauterine tube 23. Although the embodiment shown in FIGS. 1, 2a and 2b discloses a ring-shaped construction of the guiding unit 25, it will be apparent that also other closed constructions can be chosen, which surround the intrauterine tube 23. Also a guiding unit 25 having an elliptical shape is suitable for use with the intracavitary component 20.

Also shown in FIGS. 1, 2a and 2b the interstitial needle assembly 29-30 can be accommodated in the guiding unit 25 for performing radiation treatment to a targeted tumourous tissue located in or near the cervix. Each interstitial needle-assembly comprises a guidance channel 31 having a distal end 31a and a proximal end 31b. The distal guidance channel end 31a is arranged to be accommodated in the guiding unit 25, whereas the proximal guidance channel end 31b serves to interact with an insertion tool 30, as will be explained later in detail in this specification.

Interstitial needle-assembly 29-30 also consists of a hollow catheter channel having a open proximal end 32a and an closed distal end 32b. Inside the hollow catheter channel 32 a support wire 33 is accommodated, which runs until the closed distal catheter channel end 32b. The support wire 33 serves as an obturator and prevents the catheter channel 32 from damage or rupture in case of an excessive bending of the catheter channel 32 during its insertion through the hollow guidance channel 31. It also provides additional support for the catheter channel 32 as it is moved (displaced) beyond the guiding unit 25 and into the tissue.

During use, when performing radiation therapy treatment of tumour tissue inside the vaginal canal or in or near the cervix, including the parametrium the interstitial needle-assembly and especially the combined catheter channel-source wire 32-33 are guided through a guidance opening 26 present in the guiding unit 25. Usually the guiding unit 25 is provided with multiple guiding openings 26 serving to accommodate multiple interstitial needle-assemblies simultaneously for performing radiation therapy treatment at multiple positions within the treatment location inside and around the vaginal canal, including in and around the cervix.

Usually, when performing radiation therapy treatment using an assembly according to the state of the art, multiple interstitial needle-assemblies are coupled or connected to a guiding unit while the female patient is already on the table 11, awaiting the therapy treatment to be performed. This can and often does cause much discomfort for the patient. Also the known coupling principle of multiple interstitial needle-assemblies with a known guiding unit of a known assembly may result in an undesired disconnection of an interstitial needle-assembly from the guiding unit. This will alter the treatment parameters, which in turn may adversely affect the radiation treatment to be performed.

Furthermore, there is a risk when trying to guide the interstitial needles to the holes or openings in the guiding unit of causing unwanted damage or injury to the wall of the patient's body cavity, and possibly even a risk of puncturing it.

According to the invention the guiding unit 25 is provided with coupling means 27, which for coupling/uncoupling purposes are arranged in allowing a displacement of an interstitial needle-assembly 31-32-33 in a direction transverse to the longitudinal axis 25', but preventing a displacement of said guidance channel 31 in the direction parallel to said longitudinal axis 25'. In other words, the coupling principle of the guidance channel 31 with the guiding unit 25 prevents an unintended and an undesired uncoupling of the interstitial needle-assembly both in the direction parallel to the longitudinal axis 25' and also parallel to the displacement direction of an energy emitting source which is to be displaced to the catheter channel towards the tumour tissue inside the vaginal canal, when performing the radiation treatment.

As clearly shown in FIG. 2a and FIG. 2b the coupling means present on the guiding unit 25 may comprise multiple recesses 27, which are provided at specific locations in the circumferential surface of the guiding unit 25. As clearly depicted in FIG. 2a each recess 27 continues in a guiding opening 26 through which the catheter channel 32 (together with the support wire 33 accommodated inside the catheter channel) is to be guided towards a specific location in the tumour tissue to be treated.

For coupling/uncoupling purposes each guidance channel 31 is provided at its distal end 31a with a connection element 34. The connection element 34 has a shape conformal to the shape of the recess 27. An alternative to the slideable connection coupling means between recess 27 and connection means 34 could either be a simple screw thread in which the connection means 34 is provided with a male threaded portion and guiding unit 25 has a co-operating female threaded portion. A further alternative is the use of a bayonet type fixing means. Clearly, there are a number of other alternatives which could be relatively easily substituted.

More in particular and as clearly depicted in FIG. 2b each recess 27 is provided with a first recess part 27a and a second recess part 27b, whereas each connection element 34 mounted to the distal end 31a of each guidance channel 31 is provided with a corresponding first element part 34a and a second element part 34b.

First and second element parts 34a-34b have a shape conformal to the recess parts 27a-27b, such that the connection element 34 can be accommodated inside the recess 27 by displacing the guidance channel 31a in a direction transverse to the longitudinal axis 25' of the guiding unit 25. A first recess part 27a continues in the second recess part 27b, which in turn continues in the guiding opening 26. Guiding opening 26 has a diameter slightly larger then the diameter of the catheter channel 32, whereas the second recess 27b has a larger dimension than that of the first recess part 27a.

Therefore, when being accommodated the connection element 34 is located inside the recess 27 seen in the direction parallel to the longitudinal axis 25' of the guiding unit 25. The passage of the catheter channel 32 out of the end of connection element 34 and through the guiding channel 26 will lock the guidance channel 31 so preventing its transverse movement and uncoupling from the guiding unit 25.

This interlocking principle prevents an undesired and unintended uncoupling of the interstitial needle-assembly and especially the guidance channel 31 from the guiding unit 25 in a direction parallel to the longitudinal axis 25'. During use an uncoupling of the guidance channel 31 from the recess 27 is also prevented by the catheter channel 32a which is guided with the aid of the support wire 33 through the guidance channel 31 and the guiding opening 26 towards a specific location within the area around the cervix for performing radiation therapy treatment of tumour tissue inside the body cavity.

As clearly depicted in FIGS. 2a and 2b multiple recesses 27 are present in the circumferential surface of the ring-shaped guiding element 25 allowing the positioning of multiple interstitial needle-assemblies at different locations in the tumour tissue to be treated. The guiding unit according to the present invention allows for placing several interstitial needle-assemblies at different locations in order to create a more optimized radiation dose to the tumour tissue where the several catheter channels are inserted. The catheter channel 32 is made from a plastics material which is elastic and allows bending when the catheter channel is passing around a curve. Guiding support wire 33 inside the catheter channel 32 will help ensure that the catheter channel 32 will become substantially straight when it is to penetrate the tumour tissue at the desired location.

The support wire 33 is made from a particularly elastic metal (Nitinol), which enables both the support wire 33 and the catheter channel 32 to pass around curves during insertion.

As stated above the support wire 33 (or obturator) is accommodated inside the catheter channel 32 for insertion purposes prior to the actual radiation treatment. The support wire helps to prevent the catheter channel 32 from being damaged, kinked or deformed during the insertion through the guidance channel 31, the guiding hole 26 of the guiding unit 25, through the vagina canal (with its bends and curves) until the closed distal end of the catheter channel 32 reaches its desired location in the tumour tissue to be treated.

Once the catheter channel 32 has been positioned in place the support wire 33 is retracted. The catheter channel 32 which is fixed in the guidance channel 31 by connecting/ securing means 35 is connected with its proximal ends 31b-32b to a so called after loading apparatus. One or more energy emitting sources are advanced through the hollow catheter channel towards the closed distal end thereof. After the radiation treatment is completed the energy emitting source is retracted back through the catheter channel 32 towards the after loading apparatus.

Another embodiment of the guiding unit according to the invention is depicted in FIGS. 3a and 3b wherein the intracavitary component 21-23 is provided with two guiding units 250-250', each being shaped as ovoid shaped parts, which abut the intracavitary component and especially abut the intrauterine tube 23.

For mounting the ovoid guiding units 250-250' to the intrauterine tube 23 a mounting plate 255 is provided which mounting plate 255 acts as a stopper to prevent the intrauterine tube 23 going beyond its predefined depth. Each ovoid guiding unit 250-250' rests against the intrauterine tube 23. Also each ovoid guiding unit can be provided with a groove (not shown) for accommodating said intrauterine tube 23.

As depicted in FIG. 3a each ovoid guiding unit 250-250' is provided with multiple recesses 270 which each continue in a guiding opening 260 for the catheter channel-supporting wire 32-33. In a similar way as depicted in FIGS. 2a and 2b each guidance channel 31 is provided at its distal end 31a with a connecting element 34. Each connecting element 34 is as in the embodiment of FIG. 2a-2b provided with a first element part 34a and a second element part 34b which fit corresponding first and second recess parts 270a-270b.

Also in this embodiment this coupling principle allows for a displacement of the connection element 34 in the direction transverse to the longitudinal axis of the guiding unit 250-250' and prevent a displacement of the connection element 34 in the direction parallel to the longitudinal axis 25' of the guiding unit 250-250'.

It should be noted that longitudinal axis 25' of the ring guiding unit 25 is a hypothetical axis, which is considered to be parallel to the longitudinal axis of the interstitial needle-assembly 31-32-33 and more in particular parallel of the direction of insertion of an energy emitting source through the catheter channel towards the closed distal end of the catheter channel 32 at the treatment location inside the tumour tissue in the vaginal canal.

As the coupling recesses 270 are accommodated in the circumferential surface of the guiding unit 25-250-250' a gynaecological instrument is obtained, allowing additional interstitial needles to be inserted at predetermined locations/depths inside the tumour tissue from outside the patient after the intracavitary component 23 together with the guiding unit 25-250-250' is positioned inside the vaginal cavity. By using one or more interstitial needle-assemblies mounted at one or more specific recesses 270 an optimized dose distribution of radiation delivered at specific locations inside the tumour tissue can be obtained, as depicted in FIG. 4.

The benefit of the specifically shaped recesses 270 is that they allow for the preparation of the guiding unit 25-250-250' before the patient is actually being hospitalized and positioned in a treatment room (on the treatment table 11). Multiple guidance channels 31 can be positioned with their connection element 34 in the recesses 270 with the catheter channels 32 extending through the guidance channels 31 and through the guiding opening 26 as far as the distal edge of the guiding unit 25-250-250' to form a prepared guiding unit, which can subsequently be inserted together with the intrauterine tube 23 inside the vagina of the patient. Next, catheter channels 32 (provided with the support wire 33) can be pushed through the pre-positioned guidance channels 31 to the desired depths and locations inside the tumour tissue in the vagina.

FIG. 3b shows a sectional view of the ovoid guiding unit 250 of FIG. 3a. It shows the guidance channel 31 with a first connection element 34 being provided to the distal guidance channel end 31. The first connection element 34 is accommodated in a recess 270 present in the ovoid guiding unit 250. Through the guiding channel 31 a hollow catheter channel 32 is guided together with a support wire 33 being accommodated inside the hollow catheter channel 32. For an optimal support of the hollow catheter channel 32 the support wire 33 is completely accommodated inside the catheter channel 32, meaning that the distal support wire end 33b abuts against the distal catheter channel end 32b.

Also the support wire 33 will push the catheter channel 32 beyond the guidance channel 31, through the guiding bore 260 and beyond the ovoid guiding unit 250 towards an exemplar position in the tumour tissue.

A particular advantage of the present invention is also to be seen from the use of the guiding tube 31 which guides and protects the catheter channel 32. In this new assembly, the catheter channel 32 is already in place in the guiding unit 31 which is engaged with the annular ring 25, or ovoid guiding unit 250, 250' before it is inserted into the patient.

The advantages are that the physician will not have to try and insert a catheter channel into a guiding opening 26-260 in a guiding unit 25, 250, 250' in an environment in which there is relatively little or confined access. This is currently a difficult, skilled and time consuming process, which can cause the patient some discomfort. A further advantage of the present invention is the fact that the risk of a needle inadvertently or accidentally puncturing or damaging the vaginal canal or cervix during the insertion process is removed, so improving patient safety.

Traditionally, metal needles have been used in this type of applicator, but they have the disadvantage of not being compatible with MRI (magnetic resonance imaging). The present invention allows the use of a plastics material for the hollow catheter channel 32, which because it is within the guiding tube 31 is protected and so the risk of it being damaged or kinked during the insertion process is minimised. The use of the support wire 33 helps to provide the necessary stiffness for insertion of the catheter channel 32 into the soft tissue in the area of the cancer.

FIGS. 1, 5 and 6a-6b-6c disclose another aspect of the present invention.

These figures disclose an interstitial needle-assembly for performing brachytherapy treatment of tumourous tissue in a human or animal body comprising a hollow guidance channel 31 having a proximal guidance channel end 31b and a distal guidance channel end 31a provided with a connection element 34 as outlined above. Each interstitial needle-assembly 29 also comprises a hollow catheter channel 32 having an open proximal end and a closed distal end in which a support wire 33 is to be accommodated. Support wire 33 assists in inserting said catheter channel 32 through the guidance channel 31 (and a guiding unit 25-250-250') towards a desired depth and location in or near a tumourous tissue in the vaginal canal or in or around the cervix and prevents any damage to the catheter channel 32 due to an excessive bending.

Normally the exact locations and depths at which the several catheter channels 32 are to be inserted via the guiding unit of the assembly as disclosed in FIGS. 1-3 are preplanned in order to accurately and effectively perform the radiation treatment, whilst discomforting the patient to the least possible extent. It is essential that the catheter channels 32 are correctly inserted through the correct guidance channel 31 and also at the correct depth as preplanned.

In order to facilitate an easy and accurate insertion of each catheter channel 32 at the correct depth in the tumourous tissue according to the invention an insertion tool 30 is used as depicted in FIGS. 1, 5 and 6a-6c. The insertion tool or unit 30 comprises a housing 40, which is arranged for accommodating the proximal end 31b of said guidance channel 31. Hereto the proximal end 31b of the guidance channel 31 is provided with a connection/securing element 35, which consists of two parts 35a and 35b. Connection element part 35b is connected with the proximal end 31b and provided (not depicted) with an outer screw thread, which interacts with an internal screw thread provided on the coupling socket 35a, which can be screwed to the element part 35b.

Element part 35b can be fitted in the shaped portion 40b of the housing 40.

The housing 40 is provided with an open space 40a in which the proximal end 31b together with the connection element 35a-35b is to be accommodated, whilst the catheter channel 32 and the support wire 33 are pre-positioned inside the guidance channel 31. The proximal ends of the catheter channel 32 and the support wire 33 are accommodated inside the space 40a of the housing 40 and rests against an insertion plunger 41, which is movable accommodated inside the housing 40.

The insertion plunger 41 is provided with an external screw thread 41a as well as a setting nut 43 having an internal screw thread cooperating with the screw thread 41a of the plunger 41. The setting nut 43 can be adjusted by the physician in order to set the maximum displacement of the plunger 41 in the housing 40. Hereto the housing 40 is provided with a setting notch 42 to which the setting nut 43 rests once the insertion plunger 41 is displaced through the housing 40 towards the housing part 40b. Hereto both the housing 40 as well as the insertion plunger 41 are provided with gripping elements 40c and 41b respectively in order to provide sufficient grip for the fingers of the physician when operating the insertion tool 30.

By setting the maximum displacement of the insertion plunger 41 through the housing 40 by means of the setting nut 43 the maximum displacement of the catheter channel 32 and support wire 33 and more in particular the maximum displacement of the closed distal end 32b of the catheter channel relative to the tumourous tissue is herewith set in accordance with the pre-planned depth of said catheter channel. The insertion plunger 41 can be provided with a suitable scale (for example in millimeters) for setting the maximum insertion depth.

Once the catheter channel 32 together with the support wire 33 is inserted at the preset depth inside the tumourous tissue the coupling socket 35a is to be screwed tightly to the connection element part 35b in order to secure the catheter channel 32 relative to the guidance channel 31. To this end inside the space 40a a locking nut 44 is accommodated which can be shifted over the coupling socket 35a. The locking nut 44 is provided with an internal geometry conformal to the outer dimensions of the coupling socket 35a.

By shifting the locking nut 44 over the coupling socket 35a and by subsequently turning said locking nut 44 by hand (of the physician) the coupling socket 35a can be screwed tightly to the connection element part 35b thereby firmly securing the catheter channel 32 running through the guidance channel 31. Herewith an undesired displacement of the catheter channel relative to the guidance channel and the guiding unit 25-250-250' is herewith prevented.

Next the insertion tool 30 is removed and the supporting wire 33 is retracted from the catheter channel 32 which is being secured relative to the guidance channel 31.

As outlined above the catheter channel 32 can now serve for accommodating an energy emitting source, which is to be advanced from a radiation shielded compartment (of an after loading apparatus) through the catheter channel 32 towards the closed distal channel end 32b near or within the tumourous tissue to be treated.

The invention claimed is:

1. An assembly for performing brachytherapy treatment of tumour tissue in a human or animal body, comprising:
   an interstitial needle-assembly for delivering treatment to the tumour tissue and having a hollow catheter channel and a guidance channel through which the hollow catheter channel is movable,
   an intracavitary component for insertion into a body cavity, and
   a guiding unit, wherein the guiding unit has a longitudinal axis and is connectable to the intracavitary component,
   wherein the guiding unit is releasably connected to a distal end of the guidance channel by a coupler such that passage of the hollow catheter channel through a guidance opening in the guiding unit secures the guidance channel to the guiding unit, and
   wherein the guidance channel has a proximal end provided with a securing element configured to secure the hollow catheter channel against movement in a direction parallel to the longitudinal axis.

2. The assembly according to claim 1, wherein the coupler comprises at least one recess for accommodating, during use, at least part of the interstitial needle-assembly.

3. The assembly according to claim 2, and having the at least one recess provided in a circumferential surface of the guiding unit.

4. The assembly according to claim 3, in which the distal end of the guidance channel is to be accommodated in the at least one recess.

5. The assembly according to claim 4, in which the distal end of the guidance channel is provided with a first connection element fitting the at least one recess.

6. The assembly according to claim 5, in which the at least one recess comprises at least a first recess part, which continues to a second recess part and wherein the first connection element is provided with at least a first element part fitting the first recess part as well as a second element part fitting the second recess part.

7. The assembly according to claim 2, in which the at least one recess continues in the guidance opening running through the guiding unit.

8. The assembly according to claim 1, in which the guiding unit has a ring shape surrounding the intracavitary component.

9. The assembly according to claim 1, wherein the hollow catheter channel can be displaced in a direction transverse to the longitudinal axis after passage through the opening in the guiding unit.

10. The assembly according to claim 1, wherein the coupler prevents displacement of the guidance channel in a direction parallel to the longitudinal axis.

11. The assembly according to claim 1, wherein the coupler allows displacement of the guidance channel in a direction transverse to the longitudinal axis when the hollow catheter channel is removed from the guidance opening.

* * * * *

UNITED STATES PATENT AND TRADEMARK OFFICE
CERTIFICATE OF CORRECTION

PATENT NO. : 9,623,261 B2
APPLICATION NO. : 13/262629
DATED : April 18, 2017
INVENTOR(S) : Cor van de Wardt et al.

It is certified that error appears in the above-identified patent and that said Letters Patent is hereby corrected as shown below:

On the Title Page

Column 1, item (73):
"Assignee: Nucletron B.V. (NL)"
Should read:
--Assignee: Nucletron Operations B.V. (NL)--.

Signed and Sealed this
Fourteenth Day of August, 2018

Andrei Iancu
*Director of the United States Patent and Trademark Office*